United States Patent
Sagebiel

(10) Patent No.: US 9,816,966 B2
(45) Date of Patent: Nov. 14, 2017

(54) AIR BUBBLE SENSOR

(71) Applicant: ZOLL LifeBridge GmbH, Ampfing (DE)

(72) Inventor: Florian Sagebiel, Lohbarbeck (DE)

(73) Assignee: ZOLL Lifebridge GmbH, Ampfing (DE)

( * ) Notice: Subject to any disclaimer, the term of this patent is extended or adjusted under 35 U.S.C. 154(b) by 0 days.

(21) Appl. No.: 14/498,901

(22) Filed: Sep. 26, 2014

(65) Prior Publication Data
US 2015/0082863 A1    Mar. 26, 2015

Related U.S. Application Data

(63) Continuation of application No. 13/052,170, filed on Mar. 21, 2011, now Pat. No. 8,844,336.

(51) Int. Cl.
| G01N 29/02 | (2006.01) |
| A61M 5/36 | (2006.01) |
| G01N 29/22 | (2006.01) |
| A61M 1/36 | (2006.01) |
| G01N 29/032 | (2006.01) |

(52) U.S. Cl.
CPC ......... G01N 29/222 (2013.01); A61M 1/3626 (2013.01); G01N 29/032 (2013.01); A61M 2205/3375 (2013.01); G01N 2291/02433 (2013.01); G01N 2291/048 (2013.01)

(58) Field of Classification Search
CPC ........ A61M 1/3626; A61M 2205/3375; G01N 2291/02433; G01N 2291/048; G01N 29/032; G01N 29/222
See application file for complete search history.

(56) References Cited

U.S. PATENT DOCUMENTS

| 3,921,622 | A |   | 11/1975 | Cole |
| 3,974,681 | A |   | 8/1976  | Namery |
| 4,068,521 | A | * | 1/1978  | Cosentino ............. A61B 8/481 |
|           |   |   |         | 600/437 |
| 4,237,720 | A |   | 12/1980 | Abts |
| 5,177,993 | A |   | 1/1993  | Beckman et al. |
| 5,723,773 | A | * | 3/1998  | Bryan .................. G01N 29/032 |
|           |   |   |         | 310/323.18 |
| 5,811,659 | A |   | 9/1998  | Giebler |
| 5,965,089 | A | * | 10/1999 | Jarvik ................... A61M 1/101 |
|           |   |   |         | 422/44 |
| 6,142,008 | A |   | 11/2000 | Cole et al. |

(Continued)

FOREIGN PATENT DOCUMENTS

| DE | 69206209 T2 | 3/1997 |
| DE | 69927263 T2 | 6/2006 |

(Continued)

OTHER PUBLICATIONS

European Search Report dated Aug. 16, 2010 relating to European Patent Application No. 10003530.2.

Primary Examiner — Lisa Caputo
Assistant Examiner — Punam Roy
(74) Attorney, Agent, or Firm — Robert D. Buyan; Stout, Uxa & Buyan, LLP

(57) ABSTRACT

An air bubble sensor has a holder at which at least one ultrasonic sensor is arranged to detect air bubbles and/or gas bubbles in a flowing liquid, wherein a flow passage which has connection pieces is integrated into the holder.

18 Claims, 2 Drawing Sheets

(56) References Cited

U.S. PATENT DOCUMENTS

| | | |
|---|---|---|
| 6,231,320 B1 | 5/2001 | Lawless et al. |
| 6,282,949 B1* | 9/2001 | Axelsson ............ G01N 29/032 |
| | | 73/19.03 |
| 7,726,174 B2 | 6/2010 | Riley et al. |
| 7,798,996 B1* | 9/2010 | Haddad ............ A61M 5/16831 |
| | | 417/477.2 |
| 8,033,157 B2 | 10/2011 | Yardimci et al. |
| 8,091,442 B1 | 1/2012 | Dam |
| 8,225,639 B2 | 7/2012 | Riley et al. |
| 2001/0031224 A1* | 10/2001 | Labuda ................ A61B 5/0833 |
| | | 422/84 |
| 2001/0035312 A1* | 11/2001 | Han ...................... E21B 47/101 |
| | | 181/115 |
| 2003/0004458 A1* | 1/2003 | Platt ...................... A61M 5/365 |
| | | 604/65 |
| 2004/0191116 A1* | 9/2004 | Jarvik ................... A61M 1/101 |
| | | 422/44 |
| 2007/0241286 A1* | 10/2007 | Greenwald ......... A61M 1/3626 |
| | | 250/393 |
| 2008/0098798 A1* | 5/2008 | Riley .................... A61M 5/365 |
| | | 73/19.03 |
| 2008/0134750 A1 | 6/2008 | Riley et al. |
| 2009/0088687 A1 | 4/2009 | Yardimci et al. |
| 2009/0163858 A1* | 6/2009 | Haddad ............ A61M 5/16831 |
| | | 604/67 |
| 2010/0024559 A1* | 2/2010 | Bossi ................... G01N 29/043 |
| | | 73/644 |
| 2011/0197652 A1* | 8/2011 | Haddad ............ A61M 5/16831 |
| | | 73/19.03 |
| 2013/0269416 A1* | 10/2013 | Myrick ................... A61M 1/32 |
| | | 73/19.03 |
| 2014/0298888 A1* | 10/2014 | Fritsche ............... G01N 29/032 |
| | | 73/19.03 |

FOREIGN PATENT DOCUMENTS

| | | | |
|---|---|---|---|
| EP | 0524605 | A1 | 1/1993 |
| EP | 0524605 | B1 | 1/1993 |
| EP | 0778465 | A1 | 6/1997 |
| EP | 1085922 | A1 | 3/2001 |
| EP | 1085922 | B1 | 3/2001 |

* cited by examiner

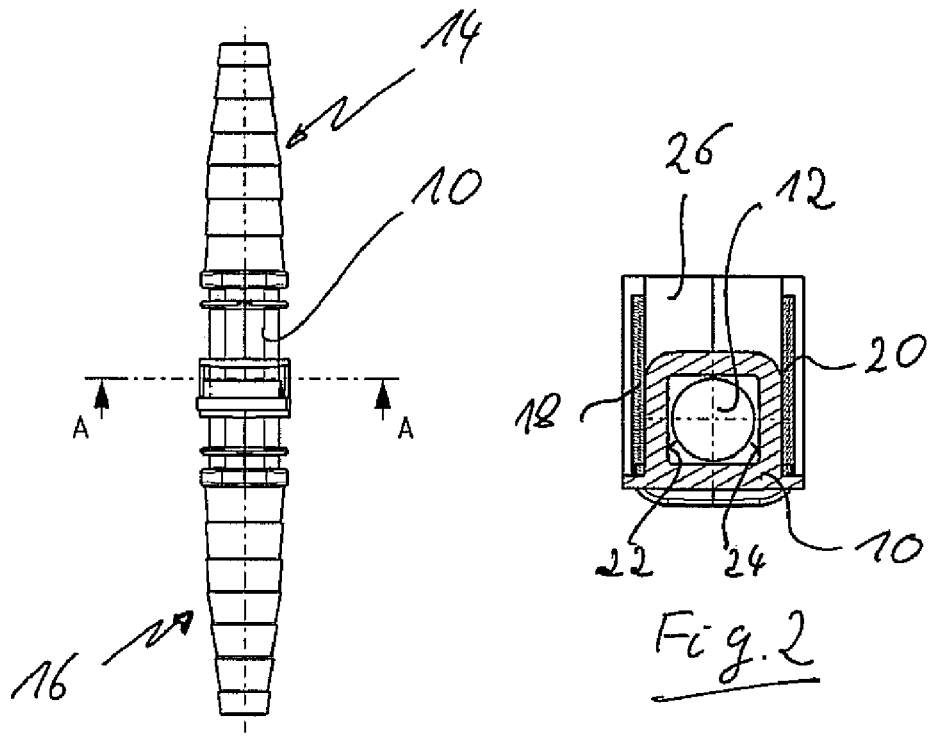
Fig. 1
Fig. 2
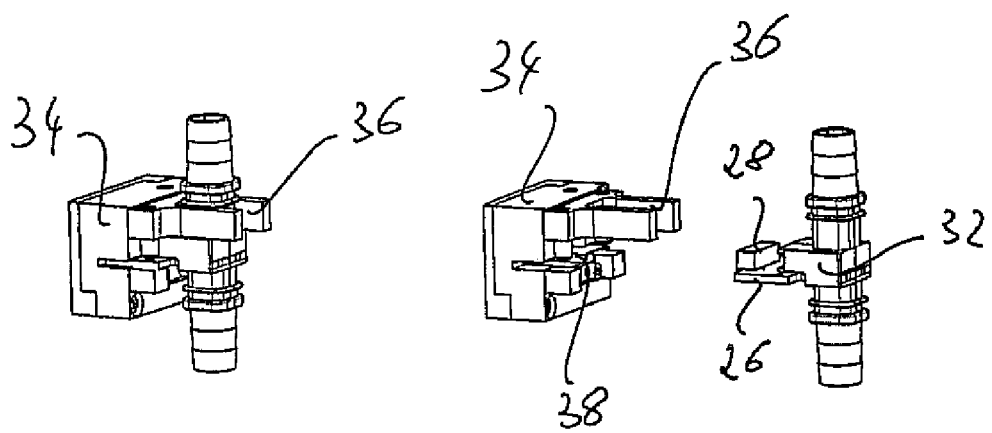
Fig. 3
Fig. 4

AIR BUBBLE SENSOR

RELATED APPLICATIONS

This application is a continuation of U.S. patent application Ser. No. 13/052,170 filed Mar. 21, 2011 and issuing as U.S. Pat. No. 8,844,336 on Sep. 30, 2014, which claims priority of European Patent Application 10003530.2 filed Mar. 31, 2010, the entire disclosure of each such prior application being expressly incorporated herein by reference.

FIELD OF THE INVENTION

The present invention relates to an air bubble sensor having a holder at which at least one ultrasonic sensor is arranged to detect air bubbles and/or gas bubbles in a flowing liquid.

BACKGROUND OF THE INVENTION

Such air bubble sensors are known from practice and serve, for example in mobile heart-lung machines, to increase the safety of the patient from air embolism. As soon as air is detected in a blood conducting tube by such an air bubble sensor, safety clamps can be activated which prevent a further conducting of air bubbles into the patient's body.

In known air bubble sensors, a blood conducting tube is inserted into the holder, which can cost valuable time in an emergency. Air bubble sensors are furthermore known in which a coupling medium has to be introduced into the holder before the insertion of the tube to improve the coupling between the air bubble sensor and the tube. This is in particular likewise time-consuming and prone to error in emergencies.

SUMMARY OF THE INVENTION

It is the object of the present invention to optimize an air bubble sensor of the initially named kind with respect to a use in emergencies. This object is satisfied by the features of the claim and in particular in that a closed flow passage is integrated into the holder, said flow passage having two connection pieces each for a respective tube. Such an air bubble sensor can be connected with the aid of the connection pieces long before use to (then) blood conducting tubes so that, when the air bubble sensor is put into operation, an insertion of a tube or even a provision of a coupling medium is not necessary. By integration of the ultrasonic sensor and of the flow passage as well as the connection pieces into the holder, a single component is provided which can in particular be configured as a disposable part and which can be disposed of after use. The air bubble sensor in accordance with the invention can be manufactured economically and can already be mounted to a mobile heart-lung machine, for example, in production; that is, it is not necessary to carry out assembly steps or adaptation when the system is first put into operation.

Advantageous embodiments of the invention are described in the description, in the drawing and in the dependent claims.

In accordance with a first advantageous embodiment, an ultrasonic sensor element, for example an ultrasonic transmitter and an ultrasonic receiver in the form of piezoceramics, can be arranged, viewed in cross-section, at two sides of the flow passage. The flow passage is hereby easily detected in a manner known per se, with no coupling media, however, having to be provided or repeatedly supplied thanks to the integration of the ultrasonic sensor elements and of the flow passage into a single component. A replacement of gel pads known from the prior art can be dispensed with and the air bubble sensor can be installed at any desired locations without good accessibility for an insertion of a tube being necessary.

In accordance with a further advantageous embodiment, the flow passage can have, at least sectionally, two oppositely disposed wall sections which extend substantially parallel to one another. In this manner, the total flow cross-section can be detected particularly easily with respect to air bubbles since the ultrasound from the—usually parallelepiped shaped—piezoceramics can be easily coupled into the interior of the flow passage.

In accordance with a further advantageous embodiment, the flow passage can—at least sectionally—have a substantially rectangular or square cross-section. Any dead zones within the flow cross-section are hereby precluded and a turbulent flow within the cross-section is avoided.

In accordance with a further advantageous embodiment, the connection pieces can be configured so that tubes having different inner diameters can be pushed onto them. In this manner, the air bubble sensor can be used universally for different tube diameters.

In accordance with a further advantageous embodiment, an electric plug connector for the ultrasonic sensor can be arranged at the holder so that said ultrasonic sensor can be coupled to a device in a particularly simple manner. Electric components to control the ultrasonic sensor can furthermore be arranged at the holder. In this manner, adaptation members and the like, which have to be matched to the sensor elements, can already be adapted during manufacture so that the air bubble sensor subsequently only has to be inserted into an associated device without further settings or adaptation measures being required.

In accordance with a further advantageous embodiment, a plug receiver for the air bubble sensor can be provided which is fastened, for example, to the device with which the air bubble sensor should be used. Such a plug receiver can in particular have a holding clamp for the air bubble sensor so that, on the preassembly, the air bubble sensor only has to be inserted into the holding clamp. After a use of the air bubble sensor, it can be removed from the plug receiver in an extremely simple manner and can, for example, be disposed of.

In accordance with an advantageous embodiment, a cut-out can be provided in the plug receiver and a plug connector of the air bubble sensor is accommodated therein in a protected manner when the air bubble sensor is plugged in. In this manner, an electric contact simultaneously takes place on a plugging of the air bubble sensor into the plug receiver, with the electric plug connector or the electric components of the aft bubble sensor being accommodated in the cut-out of the plug receiver in a protected manner.

Furthermore, in accordance with an advantageous embodiment, evaluation electronics for the air bubble sensor can be provided in the plug receiver so that an evaluation of the detected signals can take place without any long electrical lead paths in the region of the plug receiver.

In accordance with an advantageous embodiment, the air bubble sensor has a circuit board with electric or electronic components which engages around the flow passage at two sides. The sensor elements can hereby be arranged on the circuit board so that they are arranged at both sides of the flow passage after pushing the circuit board onto the holder.

It can be advantageous if the holder is configured in one piece and in particular of a material permeable for ultrasound, for example a plastic, since hereby the air bubble sensor can be manufactured particularly economically. Furthermore, the air bubble sensor can be configured as a disposable part; that is the air bubble sensor, the holder and all parts attached thereto can be disposed of after a single use.

In accordance with a further advantageous embodiment of the invention, the flow passage extends in a straight line in the throughflow direction. A turbulent flow is hereby prevented, in particular in the region of the ultrasonic sensor.

BRIEF DESCRIPTION OF THE DRAWINGS

The present invention will be described in the following purely by way of example with reference to an advantageous embodiment and to the enclosed drawings. There are shown:

FIG. 1 is a side view of an air bubble sensor;

FIG. 2 is a section through the air bubble sensor of FIG. 1 along the line A-A;

FIG. 3 is a further embodiment of an air bubble sensor which is inserted into a plug receiver;

FIG. 4 is the air bubble sensor of FIG. 3 before the insertion into the plug receiver.

DETAILED DESCRIPTION OF THE PREFERRED EMBODIMENTS

Figure 5:
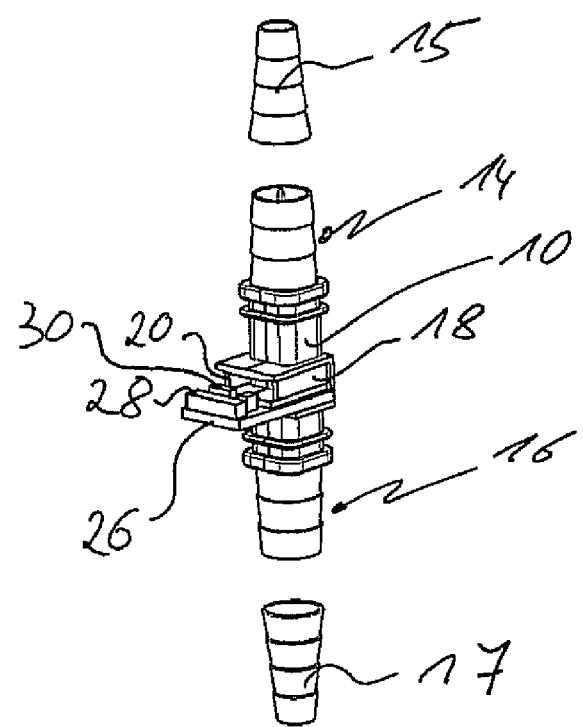
FIG. 5 is a perspective view of the air bubble sensor of FIG. 3 and FIG. 4.

The air bubble sensor shown in FIG. 1 has a holder 10 which is manufactured in one piece from plastic material and in which a flow passage 12 (cf. FIG. 2) is provided which extends in a straight line in the flow direction and which extends from one end of the holder 10 to its other end. The holder 10 has the outer contour of a tube connector and has an upper connection piece 14 and a lower connection piece 16 for one respective tube each. In the embodiment shown, the two connection pieces are configured as conically tapering and screened so that tubes having different inner diameters can be pushed onto the connection pieces. The connection pieces 14 and 16 are divided into individual conical sections having different outer diameters, which facilitates a pushing on of the tubes having different outer diameters.

FIG. 2 shows a section through the air bubble sensor of FIG. 1 along the line A-A, with it being recognizable that a respective ultrasonic sensor element in the form of piezoceramics 18 and 20 is arranged outwardly at the holder 10 at two sides of the flow passage 12, viewed in cross-section. The piezoceramics 18 and 20 have a parallelepiped platelet-shaped structure and are adhesively bonded to the holder which has, in the region of the piezoceramics 18 and 20, two oppositely disposed outer wall sections which extend in parallel to one another and to which the piezoceramics are fastened. In the region of the piezoceramics 18 and 20, that is in the region of the measurement path, the cross-section of the flow passage is configured in square form or approximately square form, whereby an ideal coupling of the ultrasonic waves into the region of the measurement path can take place. As FIG. 2 shows, the ultrasonic sensor elements 18, 20 and the oppositely disposed inner wall sections 22 and 24 of the flow passage 12 extend parallel to one another in the region of the measurement path for this purpose. The cross-section of the flow passage then merges into a round cross-section outside the measurement path.

FIG. 5 shows the air bubble sensor of FIGS. 1 and 2 in a perspective view, wherein outer end sections 15 and 17 have been removed only in the region of the connection pieces 14 and 16. For this purpose, desired break points can, for example, be provided at the end sections 15 and 17 and permit a simple removal.

FIG. 5 illustrates that a circuit board 26 is arranged beneath the ultrasonic sensor elements 18 and 20 on the air bubble sensor and its main surface extends perpendicular to the flow direction. The circuit board 26 engages around the flow passage or the measurement path at two sides so that the ultrasonic sensor elements 18 and 20 can also be fastened to the circuit board 26. A plug connector 28 which enables an electric coupling of the ultrasonic sensor is furthermore located at the front end of the circuit board 26. Electric components such as adaptation elements 30 with which a matching to the ultrasonic sensor elements used can take place are furthermore provided on the circuit board 26.

FIG. 5 illustrates that the air bubble sensor 10, the circuit board 26 as well as the components attached thereto are connected to one another to form a unit which can be handled as such; that is this unit can be preassembled in the factory after its manufacture and can be connected to corresponding tubes. After use, the unit can be unplugged from the tubes and disposed of.

FIGS. 3 and 4 show the air bubble sensor of FIG. 5, wherein a panel 32 is only provided in the region of the sensor elements 18 and 20. FIGS. 3 and 4 furthermore show a plug receiver 34 for the air bubble sensor which has a holding clamp 36 into which the air bubble sensor can be plugged. A cut-out 38 is furthermore provided in the plug receiver 34 and the plug connector 28 as well as the circuit board 26 are accommodated therein in a protected manner with a plugged in air bubble sensor. A complementary plug part is also located within the plug receiver 34 so that not only a mechanical fastening, but also simultaneously an electrical contacting has taken place after insertion of the air bubble sensor into the plug receiver. Evaluation electronics (not shown) for the air bubble sensor are furthermore provided in the plug receiver 34.

The air bubble sensor in accordance with the invention can be integrated directly into a tube system without a coupling to the tube system via a coupling medium having to take place. There is thus no need for the error-prone insertion of a tube and the application of a coupling medium. The air bubble sensor is ready for use directly after the installation and the air bubble sensor can also be positioned at inaccessible points. The sensor can be removed from the plug receiver after utilization and one-time use and can be disposed of with the other tube material. The evaluation electronics can, however, remain in the plug receiver and be utilized again for the following use. The plug receiver can be fastened to the housing of a desired device, for example of a heart-lung machine.

What is claimed is:

1. A system comprising an air bubble sensor assembly and a plug receiver, wherein:
    the air bubble sensor assembly comprises a holder having a flow passage extending therethrough, a first tubing connector formed on one end of the flow passage and a second tubing connector formed on another end of the flow passage and at least one ultrasonic sensor arranged on the holder to detect air bubbles and/or gas bubbles in a liquid that flows through the flow passage of the holder, said ultrasonic sensor comprising ultrasonic transducer elements positioned on opposite sides of the flow passage and a circuit board and a plug connector; and the plug receiver is mountable in an extracorporeal blood treating device, said plug receiver being configured to electrically couple with the plug connector of the air bubble sensor assembly, wherein the plug receiver includes a holding clamp which holds the ultrasonic sensor assembly in place within an extracorporeal blood treating device in which the plug receiver is mounted, when so mounted, and wherein the plug receiver is configured such that insertion of the air bubble sensor assembly into the holding clamp results in electrical coupling of the plug connector with the plug receiver, and wherein evaluation electronics for the bubble sensor are provided in the plug receiver.

2. A system in accordance with claim 1, wherein at least a measurement region of the flow passage has a square or near-square cross-sectional configuration.

3. A system in accordance with claim 1, wherein the flow passage has, at least sectionally, two oppositely disposed wall sections which extend substantially parallel to one another.

4. A system in accordance with claim 1, wherein the first and second tubing connectors are configured so that tubes having different inner diameters can be pushed onto them.

5. A system in accordance with claim 1 wherein said extracorporeal blood processing device comprises a heart-lung machine.

6. A system in accordance with claim 1, wherein a cut-out is provided in the plug receiver and the plug connector and all electronic components of the bubble sensor reside(s) within said cut-out in a protected manner while the bubble sensor is in use.

7. A system in accordance with claim 1, wherein the flow passage extends in a straight line between the first and second tubing connectors so as to prevent turbulent flow in the region of the ultrasonic sensor.

8. A system in accordance with claim 1, wherein the ultrasonic sensor is integrated with the flow passage in a manner that precludes any requirement for the use of gel or other ultrasonic coupling medium.

9. A system in accordance claim 1, wherein the ultrasonic transducer elements comprises first and second piezoceramics positioned on opposites sides of the flow passage.

10. A system in accordance with claim 1, wherein the holder is configured in one piece and formed of ultrasound-permeable material.

11. An air bubble sensor comprising:
an assembly comprising a holder having a flow passage extending therethrough, a first tubing connector formed on one end of the flow passage and a second tubing connector formed on another end of the flow passage and at which at least one ultrasonic sensor is arranged on the holder to detect air bubbles and/or gas bubbles in a liquid that flows through the flow passage of the holder, said ultrasonic sensor comprising ultrasonic transducer elements positioned on opposite sides of the flow passage and a circuit board and a plug connector; and a plug receiver which electrically couples with the plug connector of the ultrasonic sensor;

wherein evaluation electronics for the bubble sensor are provided in the plug receiver; and wherein the ultrasonic sensor is integrated with the flow passage in a manner that precludes any requirement for the use of gel or other ultrasonic coupling medium.

12. An air bubble sensor in accordance with claim 11, wherein at least a measurement region of the flow passage has a square or near-square cross-sectional configuration.

13. An air bubble sensor in accordance with claim 11, wherein the flow passage has, at least sectionally, two oppositely disposed wall sections which extend substantially parallel to one another.

14. An air bubble sensor in accordance with claim 11, wherein the first and second tubing connectors are configured so that tubes having different inner diameters can be pushed onto them.

15. An air bubble sensor comprising:
an assembly comprising a holder having a flow passage extending therethrough, a first tubing connector formed on one end of the flow passage and a second tubing connector formed on another end of the flow passage and at which at least one ultrasonic sensor is arranged on the holder to detect air bubbles and/or gas bubbles in a liquid that flows through the flow passage of the holder, said ultrasonic sensor comprising ultrasonic transducer elements positioned on opposite sides of the flow passage and a circuit board and a plug connector; and a plug receiver which electrically couples with the plug connector of the ultrasonic sensor;

wherein evaluation electronics for the bubble sensor are provided in the plug receiver; and wherein the holder is configured in one piece and formed of ultrasound-permeable material.

16. An air bubble sensor in accordance with claim 15, wherein at least a measure region of the flow passage has a square or near-square cross-sectional configuration.

17. An air bubble sensor in accordance with claim 15, wherein the flow passage has, at least sectionally, two oppositely disposed wall sections which extend substantially parallel to one another.

18. An air bubble sensor in accordance with claim 15, wherein the first and second tubing connectors are configured so that tubes having different inner diameters can be pushed onto them.

* * * * *